United States Patent [19]
Honzawa et al.

[11] Patent Number: 5,637,874
[45] Date of Patent: Jun. 10, 1997

[54] APPARATUS AND METHOD FOR MEASURING CHEMILUMINESCENCE

[75] Inventors: Katsu Honzawa; Kazuhiro Atsumi; Fumihiko Shimomura; Masayuki Masuko; Tsuyoshi Hayakawa, all of Hamamatsu, Japan

[73] Assignee: Biosensor Laboratories Co., Ltd., Tokyo, Japan

[21] Appl. No.: 393,387

[22] Filed: Feb. 23, 1995

[30] Foreign Application Priority Data

Dec. 20, 1994 [JP] Japan ................... 6-316667

[51] Int. Cl.⁶ ........................... G01N 21/76
[52] U.S. Cl. ......................... 250/361 C; 422/52
[58] Field of Search ............... 250/361 C; 422/52

[56] References Cited

U.S. PATENT DOCUMENTS

| | | |
|---|---|---|
| 4,213,703 | 7/1980 | Haunold et al. ........... 250/361 C |
| 5,223,218 | 6/1993 | Fukuoka et al. ........... 250/361 C |

FOREIGN PATENT DOCUMENTS

| | | |
|---|---|---|
| 0314448 | 5/1989 | European Pat. Off. . |
| 63-161351 | 10/1988 | Japan . |
| 1229944 | 9/1989 | Japan . |
| 429040 | 1/1992 | Japan . |
| 2211607 | 7/1989 | United Kingdom . |

*Primary Examiner*—Carolyn E. Fields
*Attorney, Agent, or Firm*—Cushman Darby & Cushman, IP Group of Pillsbury Madison & Sutro, LLP

[57] ABSTRACT

The present invention provides a chemiluminescence measuring apparatus which is small in size and high in operability and has a function of performing accurate quantitative analysis and the like. The apparatus includes at least a box-like housing having an opening, a cover provided on a top surface of the housing and having a through hole for introducing a first detachable vessel into the inner space of the housing, a holder having a concave portion and enclosing the opening of the housing, the hollow chamber having an opening at a side wall thereof and partially housing a second vessel, a photo-sensing unit for detecting luminescence from the second vessel via the through hole of the hollow chamber, and a shutter mechanism for intermittently cutting optical path between the photo-sensing unit and the second vessel. Particularly, the shutter mechanism includes a rotatable hollow chamber partially housing the vessel, provided in the hollow chamber and having an opening at a side wall thereof, and a driving motor rotating the rotatable hollow chamber.

17 Claims, 7 Drawing Sheets

APPARATUS AND METHOD FOR MEASURING CHEMILUMINESCENCE

BACKGROUND OF THE INVENTION

1. Field of the Invention

The present invention relates to an apparatus and a method for quantitatively analyzing the composition and the like of a sample solution by measuring luminescence such as bioluminescence or chemiluminescence caused when the sample solution and a luminous reagent are mixed with each other.

2. Related Background Art

Consider a case wherein a luminous reagent is mixed with a sample solution obtained by mixing organism cells or a sample solution containing chemical substances, and the sample solution is quantitatively analyzed by measuring luminescence from the sample solution which is caused by this mixing operation. Generally, in this case, when this luminescence continues for a long period of time (i.e., the duration of the luminescence is long), a researcher or the like can perform measurement after one mixes the luminous reagent with the sample solution outside the chemiluminescence measuring apparatus and stores the solution mixture in the apparatus. However, when a sample solution which causes luminescence for only a short duration is to be measured, accurate quantitative analysis cannot be realized by the luminescence measuring apparatus if a measuring operation is performed according to the above procedure. The apparatuses for measuring the sample solution which causes luminescence for only a short duration are described, for example, in Laid-Open Japanese Patent Applications No. 4-29040 and No. 1-22994, and Laid-Open Japanese Utility model Application No. 63-161351.

SUMMARY OF THE INVENTION

An object of the present invention relates to providing a luminescence measuring apparatus which is small in size and high in operability, and has a function of performing accurate quantitative analysis and the like. Further, the present invention relates to a method for performing accurate quantitative analysis which is superior to the conventional technique.

In order to achieve the above objects, an luminescence measuring apparatus of the present invention comprises a first holding mechanism provided at a cover so as to hold a first vessel, such as a sample syringe containing luminous reagent, and a second holding mechanism provided in a box-like housing so as to hold a second vessel containing a sample solution independently. The detailed structure of the apparatus is shown in FIGS. 1, 2 and 8. The apparatus of the present invention comprises: a box-like housing 1 having an opening 15 at a top surface thereof; a cover 6 provided at the top surface of the housing 1, the cover 6 having a through hole 24 that allows a distal end of a sample syringe 42 as first vessel containing a luminous reagent to be introduced into the interior of the housing 1; a hollow chamber 33 being disposed in the housing 1 and having an opening 38 at a side wall thereof, the hollow chamber 33 having an inner space that allows a micro-sample tube 21 to be partially housed as a second vessel containing a sample solution; a holder 16 being disposed in the housing 1 and enclosing the opening 15 of the housing 1, the holder 16 having a concave portion 200 for forming a first space 20 defined with the cover 6 and having a through hole 22 connecting the first space 20 to the inner space of the hollow chamber 33 at a bottom surface of the concave portion 200; a photo-sensing unit 40 being disposed in the housing 1, for detecting luminescence from the second vessel 21 via the opening 38 of the hollow chamber 33; and a shutter mechanism for optically shielding luminescence from the micro-sample tube 21. The housing 1, the cover 6, the hollow chamber 33 and the holder 16 are made of nontransparent material.

In particular, the shutter mechanism comprises: a rotatable hollow chamber 370 made of a nontransparent material, as the second holding mechanism, for holding the micro-sample tube 21 at a predetermined position while partially housing the micro-sample tube 21 therein, the rotatable hollow chamber 370 being disposed in the hollow chamber 33 and having an opening 37 at a side wall thereof; and a driving motor 36 as a rotator for rotating the rotatable hollow chamber 370, the driving motor 36 being disposed in the hollow chamber 33 while holding the rotatable hollow chamber 370.

In other words, the shutter mechanism includes a rotating cylindrical member 370 which houses the vessel 21, is housed in the hollow chamber 33 in the dark box portion (housing 1), and has an opening 37 at a side wall thereof, an optical path between the vessel 21 and the photo-sensing unit 40 (including a photomultiplier) is opened when the opening 37 of the rotating cylindrical member 37 coincides with the opening 38 of the hollow chamber 33 upon rotation of the rotating cylindrical member 370, and the opening 38 of the hollow chamber 33 is closed when the openings 37, 38 of the rotating cylindrical member 370 and the hollow chamber 33 do not coincide with each other, thereby realizing a shutter function.

As shown in FIG. 2, the first holding mechanism of the present invention comprises a guide member 27 which is disposed in the first space 20 and which contacts the cover 6 to define a second space 201 with the cover 6, the guide member 27 having a through hole 28 that allows the distal end of the sample syringe 42 to be introduced into the micro-sample tube 21. For detecting existence or absence of the micro-sample tube 21, in the second space 201, a photodiode 26 and a laser-emitting diode 25 are provided. Further, an O-ring 29, as a stopper for holding the sample syringe 42 at a predetermined position, is disposed in the first space 20 and has a through hole 290 that allows the distal end of the sample-syringe 42 to be partially introduced into the micro-sample tube 21. A diameter (W3) of the through hole 290 of the O-ring 29 is smaller than that (W2) of the through hole 28 of the guide member 27, and the diameter (W2) of the through hole 28 of the guide member 27 is smaller than that (W1) of through hole 24 of the cover 6.

The apparatus of the present invention further comprises a first optical sensor 39 for detecting the existence or absence of the micro-sample tube 21 and a second optical sensor 31 for detecting an open or closed state of the cover 6. The first optical sensor 39 is mounted with passing through the side wall of the hollow chamber 33, and the second optical sensor 31 is disposed at a portion facing to the cover 6, especially the portion is included in the concave portion 200 of the holder 16.

A seal member 23, mounted at the opening 22 of the holder 16, functions to seal the inner space of the hollow chamber 33 and support the micro-sample tube 21.

The apparatus of the present invention further comprises a chip guide 30, being a hollow member that can be detachably mounted in the through holes 24, 28 of the cover 6 and the guide member 27, and a chip member 43 attached to a predetermined portion of the sample syringe 42.

A method for measuring chemiluminescence comprises in steps of: disposing the micro-sample tube 21 containing a sample solution in a black box-like housing 1 that includes a through hole 24 positioned at a top surface thereof; thereafter, introducing the distal end of the sample syringe 42 on which the chip member 43 is mounted into the inner space of the micro-sample tube 21 via the detachable chip guide 30 mounted in the through hole 24 of the housing 1. Since the chip guide 30 is a hollow member made of a nontransparent material and the chip member 43 is made of a nontransparent material, the chip guide 30 and chip member 43 seal the housing 1 when the chip guide 30 is in contact with the chip member 43 by introducing the distal end of the sample syringe 42 via the chip guide 30 into the interior of the housing 1.

Thereafter, the method of the present invention performs sealing of the interior of the housing 1 by forming a in tight contact between the chip member 43 and the chip guide 30, and detecting luminescence from the micro-sample tube 21 in which the luminous regent is infused, by a photomultiplier. In particular, the method of the present invention performs a detecting step while optically shutting luminescence from the micro-sample tube 21 for a predetermined time interval.

As described above, the apparatus of the present invention has a structure which is attachable and detachable from the sample syringe 42 and which is also attachable and detachable from the micro-sample tube 21.

If a sample solution may scatter and adhere to the tank, the tube, and other mechanisms, or microorganisms may propagate in sample solution deposits to serve as contaminant sources, such contaminant sources interfere with luminescence from the above solution mixture or become unnecessary luminescence sources, thereby interfering with accurate quantitative analysis. The apparatus of the invention prevents propagation of undesirable various germs.

Although, the previous luminous reagent must be completely removed when a luminous reagent different in type from a previous luminous reagent is to be used, the invention does not necessitate the above cleaning.

Further, since the apparatus of the present invention does not require the first or second vessel to be moved, the apparatus does not has an automatic injecting mechanism. Therefore, the overall chemiluminescence measuring apparatus is small in size and superior in terms of operability and installation.

In performing quantitative analysis, the vessel in which a sample solution is stored is housed in the hollow chamber in the dark box portion (housing made of nontransparent material), and the chip member is mounted on the chip guide to set the sample solution in a perfectly dark state. The optical path between the second vessel and the photo-sensing unit is opened by the shutter mechanism to allow detection of luminescence from the sample solution. A luminous reagent stored in the chip member in advance is poured (injected) into the second vessel by operating the reagent syringe. As a result, luminescence from the sample solution is detected. In addition, a change in luminescence over time can be measured in real time by displaying the luminescence on a monitor or the like on the basis of a signal output from the photo-sensing unit.

The present invention will become more fully understood from the detailed description given hereinbelow and the accompanying drawings which are given by way of illustration only, and thus are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art form this detailed description.

DETAILED DESCRIPTION OF THE PREFERRED EMBODIMENTS

Figure 1:
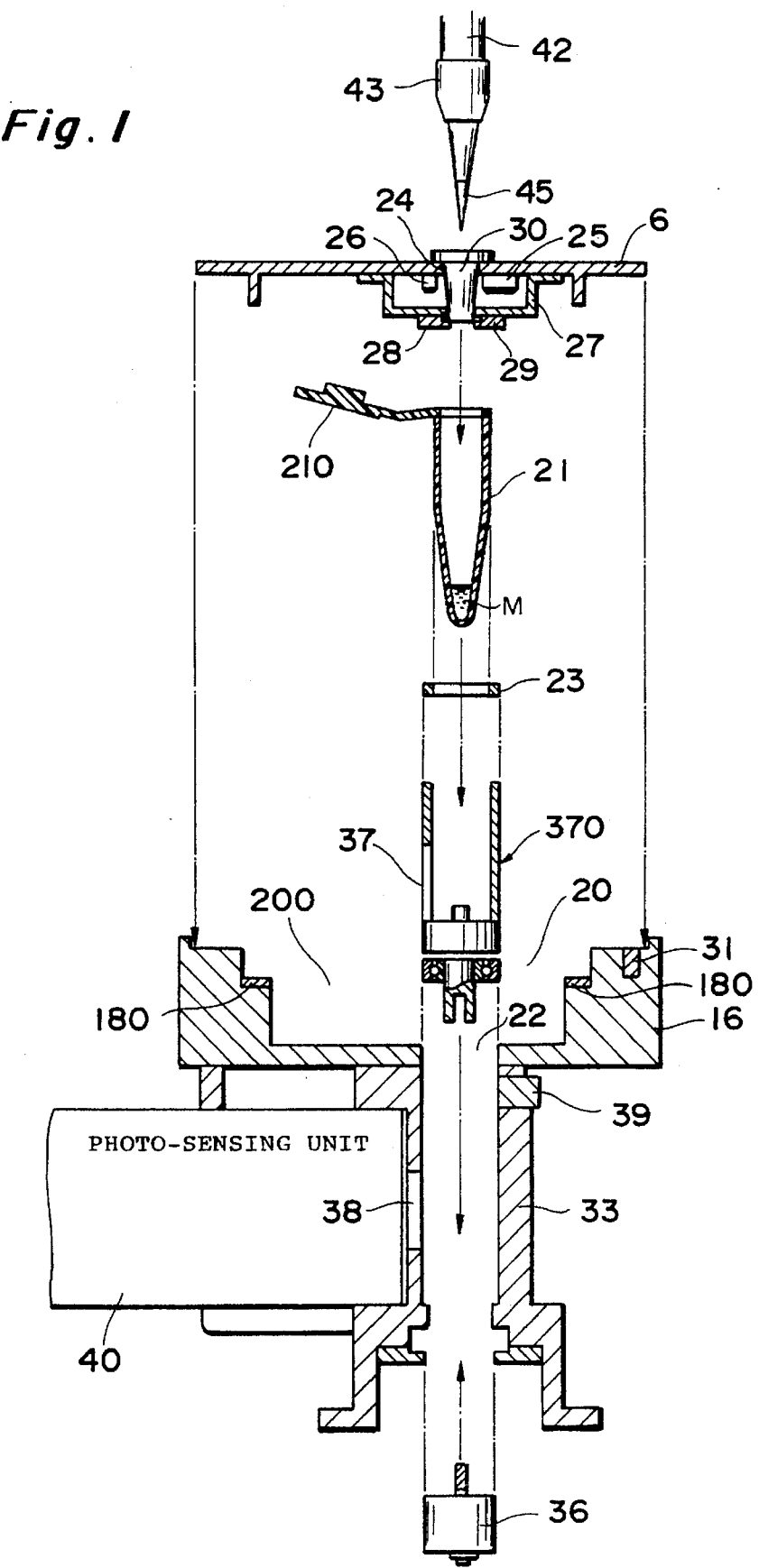
FIG. 1 is a sectional view showing a structure of an apparatus for measuring chemiluminescence according to an embodiment of the present invention.
Figure 2:
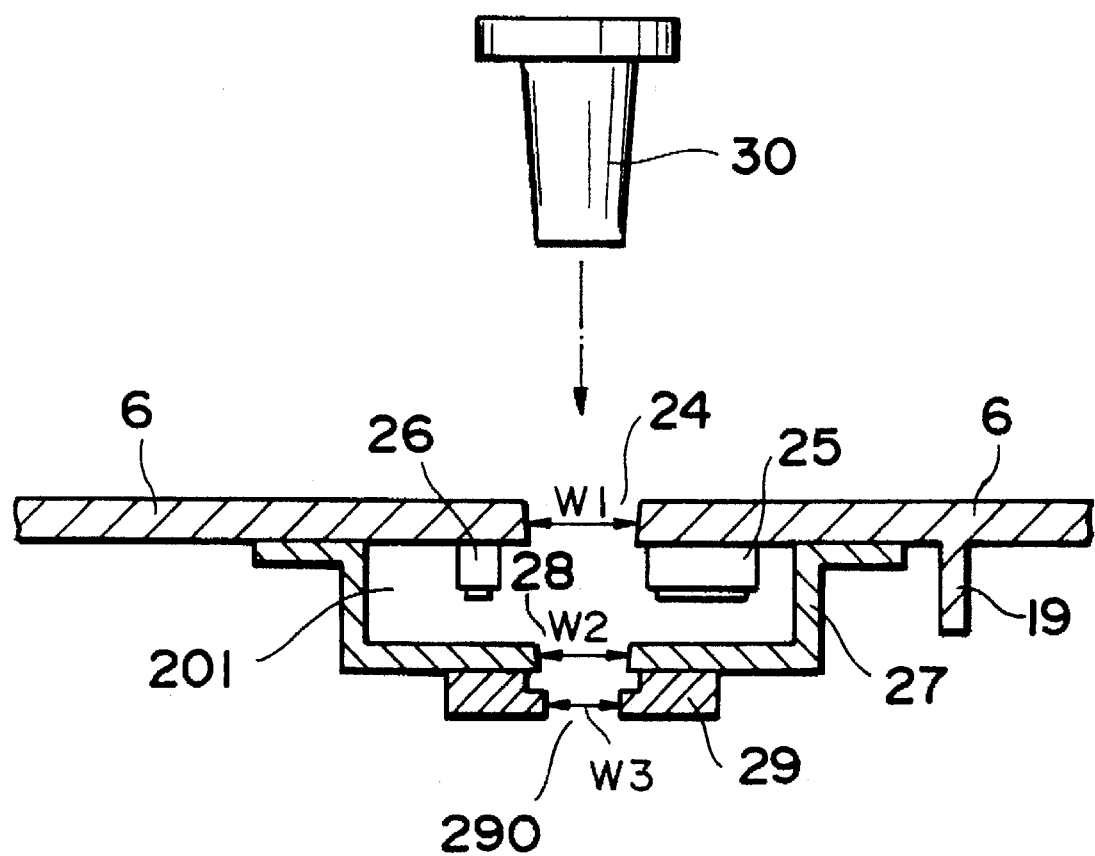
FIG. 2 is a sectional view showing the structure of the cover of the apparatus in FIG. 1.
Figure 3:
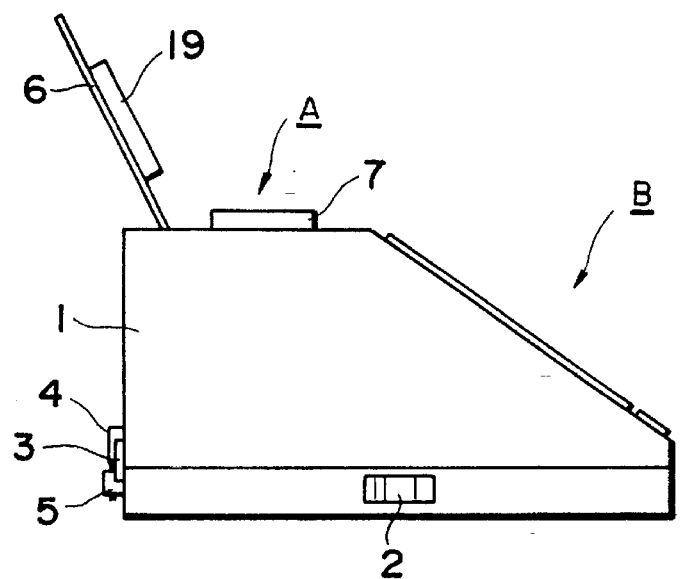
FIG. 3 is a side view showing the outer shape of a chemiluminescence measuring apparatus according to an embodiment of the present invention.
Figure 4:
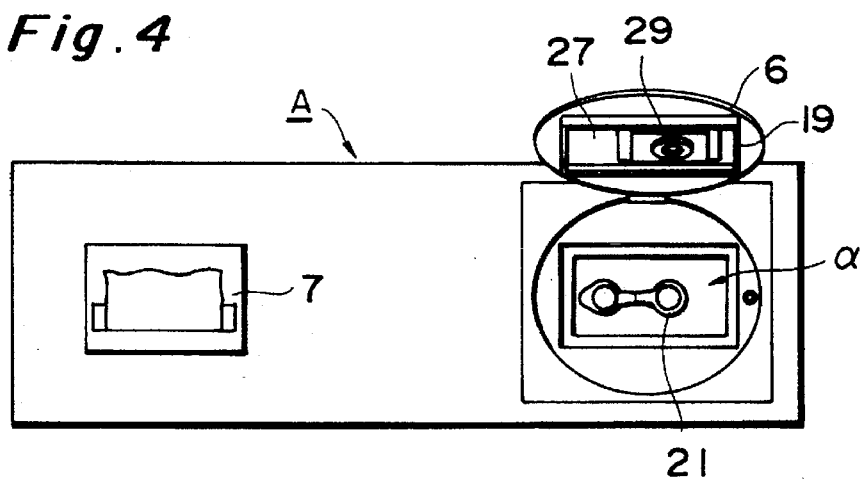
FIG. 4 is a top view showing the structure of a main portion arranged on the upper portion of the apparatus of the embodiment.
Figure 5:
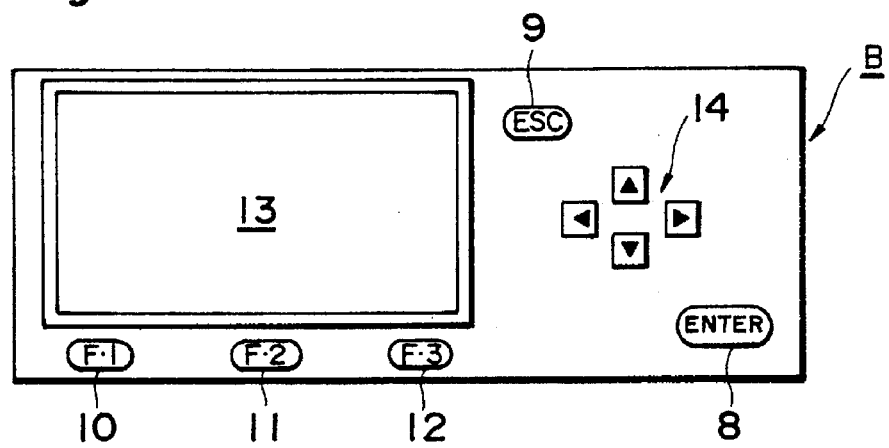
FIG. 5 is a front view showing the structure of a main portion arranged on the front portion of the apparatus of the embodiment.

A chemiluminescence measuring apparatus of an embodiment will be described below with reference to the accompanying drawings. The outer structure of the apparatus will be described first with reference to FIGS. 3 to 5. FIG. 3 is a side view of the apparatus. FIG. 4 is a top view showing the structure of a main portion arranged on the upper portion of the apparatus. FIG. 5 is a plan view showing the structure of a main portion arranged on the front surface of the apparatus.

Referring to FIG. 3, a power switch 2 for turning on/off a commercial AC power supply is arranged on a side surface of a box-like housing 1. An input/output port is arranged on the rear surface of the housing 1. The input/output port includes an electrical outlet 3 for connection of a power cable, a connector 4 conforming to the RS232C standard and designed to exchange data with an external computer system and various measuring devices (not shown), an external connector (coaxial connector) 5 for outputting a detection signal, which is generated in a measuring operation (to be described later), to the above computer system and various measuring devices, and the like.

A cover 6 is swingably provided on the top surface of the housing 1 by a hinge mechanism 160.

In addition, as shown in FIG. 4, a mount portion α (a concave portion of the holder 16) on which a micro-sample tube 21 (to be described later) is to be mounted is arranged on an upper portion A of the housing 1. As shown in FIG. 4, the mount portion α is exposed to the outside when the cover 6 is opened, and is shielded from the outside when the cover 6 is closed. A printer 7 is incorporated in the upper portion A of the housing 1. The printer 7 prints, for example, a plot or numerical values to indicate a change in the above detection signal over time.

Furthermore, as shown in FIG. 5, an operation panel is arranged on an inclined surface B of the front surface of the housing 1. The operation panel includes a control key 8 for instructing a measuring mechanism (to be described later) incorporated in the housing 1 to execute measurement, a cancel key 9 for stopping the execution halfway, function keys 10, 11, and 12 for selecting various measuring operations (measurement 5 menu), a liquid crystal display 13, a multifunction key 14, and the like.

Figure 6:
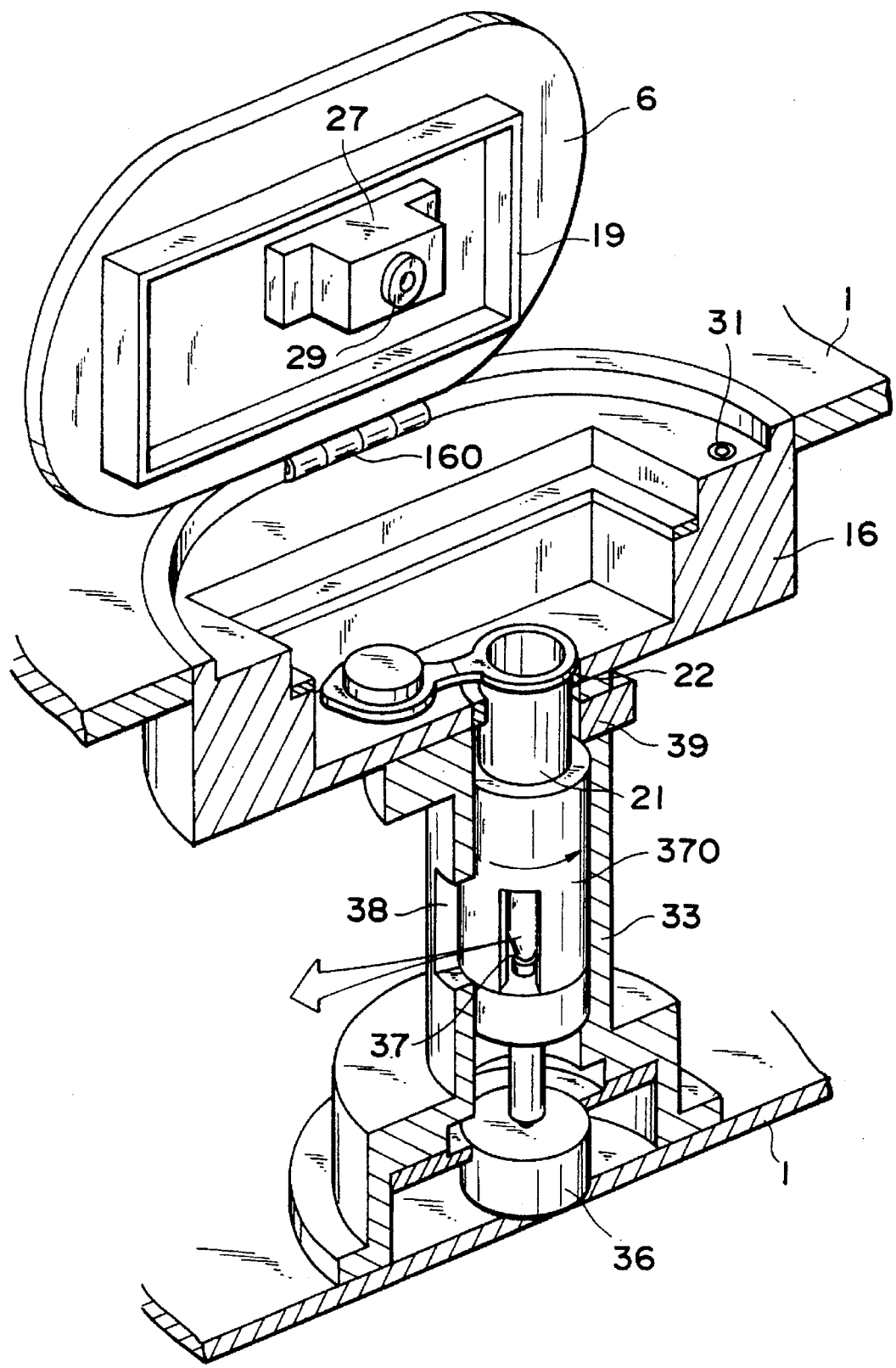
FIG. 6 is a sectional view showing the structure of a shutter mechanism of the embodiment.

Next, FIG. 6 shows the structure of a shutter mechanism of an embodiment of the invention. The apparatus for measuring chemiluminescence comprises a box-like housing 1 as a casing for the shutter mechanism and photo-sensing mechanism. The housing 1 is made of nontransparent material and has an opening 15 at a top surface thereof. The cover 6 is provided at the top surface of the housing 1 and is in contact with the guide member 27 having a through hole. Further, a projection 19 is provided on inside surface of the cover 6, and the O-ring as a stopper having a through hole is provided on the surface of the guide member 27 as shown in FIG. 6. Since the through hole of the O-ring 29 has a smaller diameter than the cover 6, the O-ring 29 holds the guide member 30 which is a tapered hollow member (Wi>W3), thereby the luminous reagent syringe 42 is held at a predetermined position.

As shown in FIG. 6, the hollow chamber 33 is disposed in the housing 1 and has the opening 38 at a side wall thereof, therefore an inner space of the hollow chamber 33 allows to partially house a micro-sample tube 21 containing a sample solution. The holder 16 is disposed on the hollow chamber 33 and has the through hole 22 connecting the inner space (the hollow space 32) of the hollow chamber 33 to the space 20. The distal end of the luminous reagent syringe 42 is partially inserted into the inner space of the hollow chamber 33 via the through hole of the holder 16. The rotating cylindrical hollow chamber 370 having an opening 37 and the driving motor 36 rotating the chamber 370 are disposed in the hollow chamber 33, and the optical path between the photo-sensing unit 40 and the luminous reagent syringe 42 is opened when the position of the opening 38 and the position of the opening 37 coincide with each other.

Figure 7:
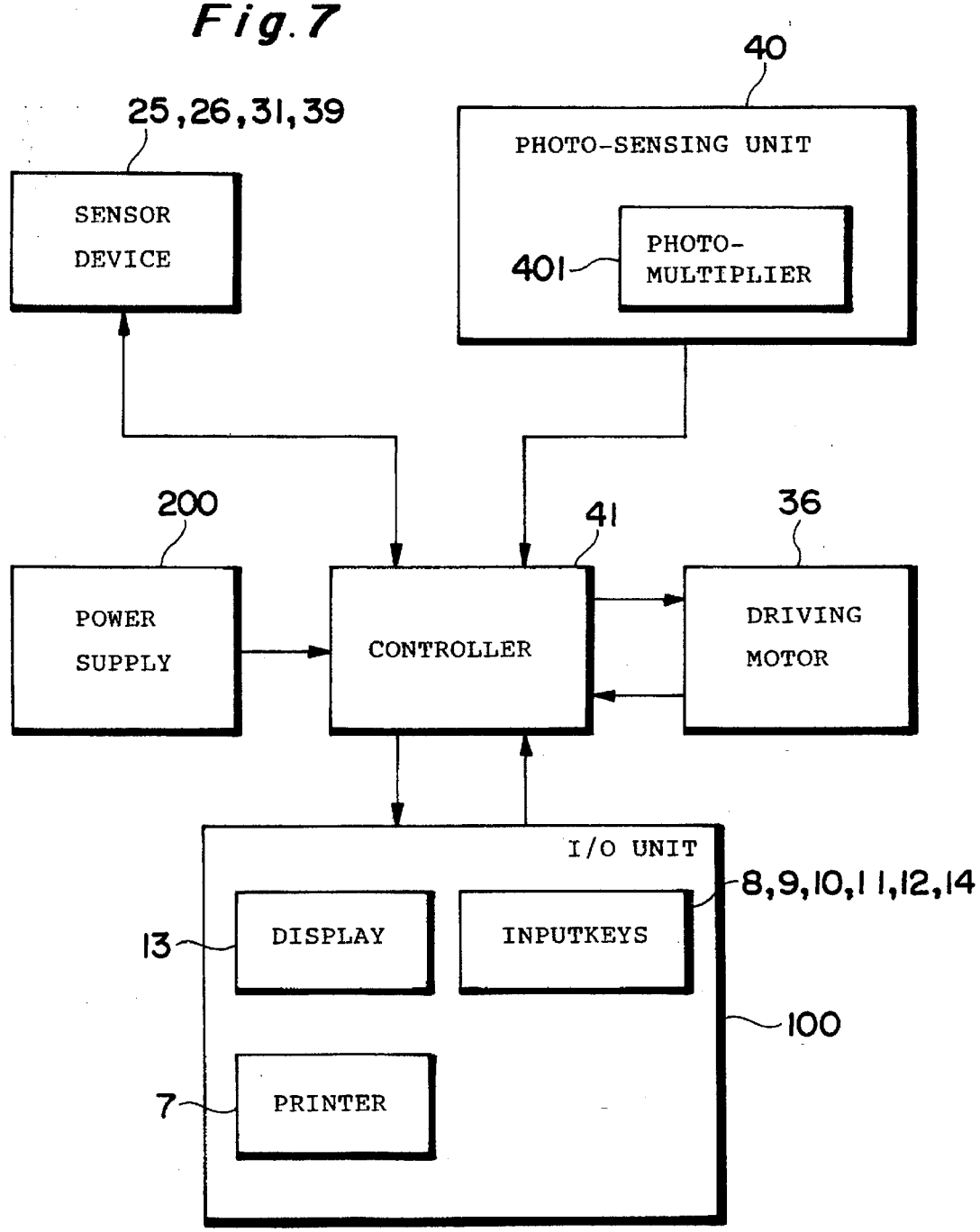
FIG. 7 is a block diagram showing the control system of an embodiment of the present invention.

FIG. 7 shows a control system of the embodiment of the present invention. The controller 41 is supplied power from the power supply 200 and observes the signals from sensors 26, 31 and 39 as sensor devices. For example, if the controller 41 receives signals from the photodiode 26, the guide member 30 will exist; if the controller 41 receives signals from the optical sensor 31, the cover 6 will be closed; if the controller 41 receives signals from the optical sensor 39, the luminous reagent syringe 42 will exist; if the controller does not receive signals from one or more of the sensors 26, 31 and 39, the controller 41 displays a predetermined message on the liquid crystal display 13 in I/O unit 100.

The controller 41 performs measuring of chemiluminescence after receiving the instruction signals from various input keys 8, 9, 10, 11 and 12 of I/O unit 100. In measuring chemiluminescence, the controller 41 outputs the instruction signals to move the driving motor 36, thereby the shutter mechanism intermittently shuts the optical path between the photo-sensing unit 40 and the micro-sample tube 21. After the photo-sensing unit 40 intermittently receives luminescence from the micro-sample tube 21 by the photomultiplier 401, the controller 41 outputs signals as measuring result to I/O unit 100 in order to display the data on the liquid crystal display 13 or print the data with the printer 7.

Figure 8:
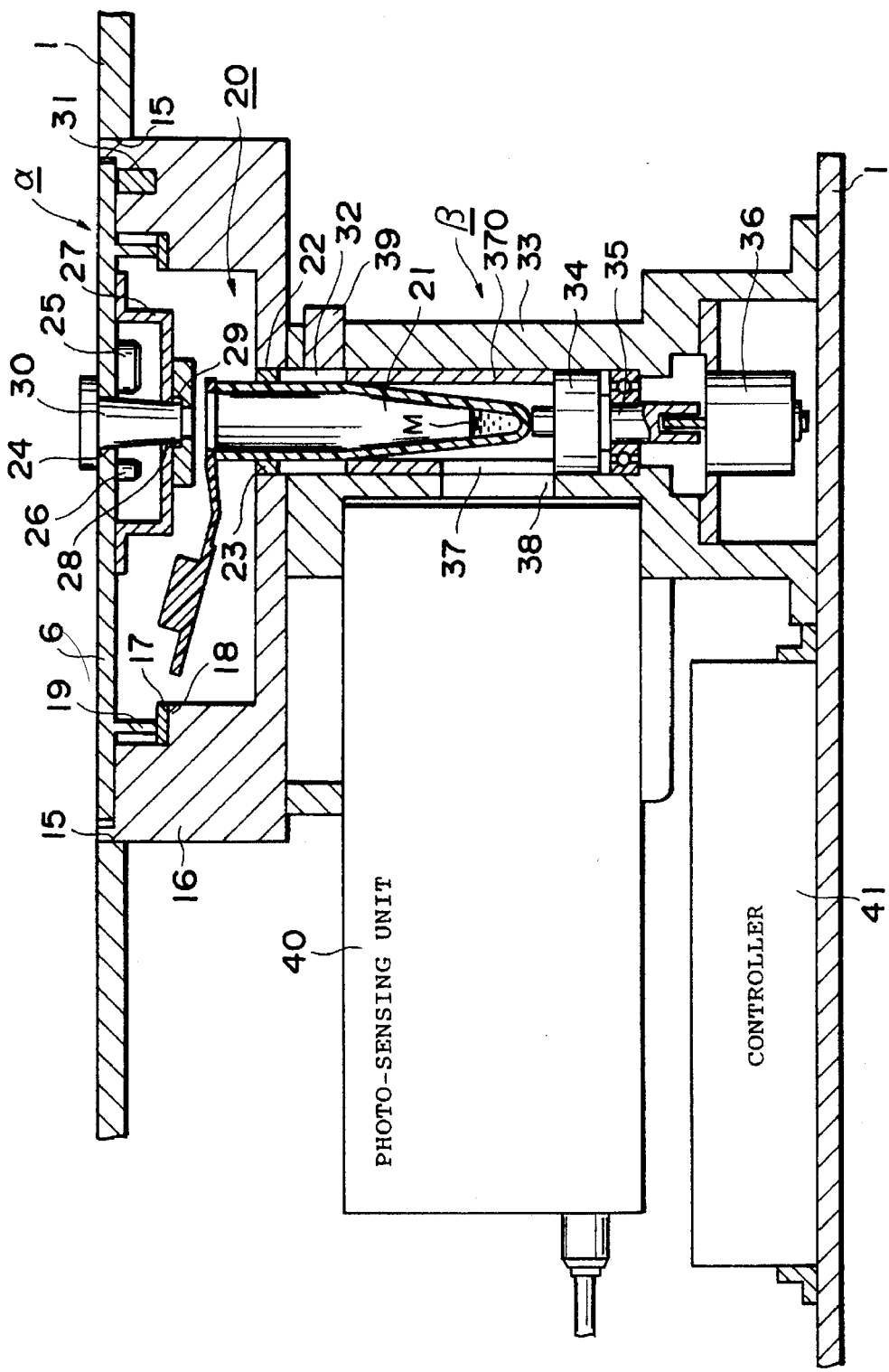
FIG. 8 is a sectional view showing the internal structure of the apparatus of the embodiment.

The arrangement of the measuring mechanism arranged in the apparatus will now be described next with reference to FIG. 8. Note that the measuring mechanism is constituted by a plurality of portions having different functions, and includes the mount portion α (the concave portion of the holder 16) on which the micro-sample tube 21 is to be mounted, and a photosensing mechanism β for detecting luminescence from a sample solution in the micro-sample tube 21.

The arrangement of the mount portion a will be described. A substantially cup-like holder 16 is fixed in a hole 15 formed in the upper portion of the housing 1, and the concave portion of the holder 16 is 5 opened/closed by the cover 6 provided on one end of the holder 16 by the hinge mechanism 160. A stepped portion 18 on which a seal member 17 consisting of a rubber material or the like having relatively high viscosity is formed on the inner wall of the holder 16. When the cover 6 is closed, a projection 19 extending from the inner side of the cover 6 is engaged with the stepped portion 18 and brought into slight contact with the seal member 17, thereby preventing leakage of external light into an internal space 20 of the holder 16 via the above engaging portion.

A through hole 22 in which the micro-sample tube 21 is to be fitted is formed in the bottom surface of the holder 16. The micro-sample tube 21 is an elongated vessel consisting of a transparent or semitransparent material, which transmits light. That is, the micro-sample tube 21 is an elongated vessel in the form of a test tube, which is used to store a sample solution or the like in a chemical experiment.

A through hole 24 is formed in the cover 6 to oppose the through hole 22 while the concave portion of the holder 16 is closed by the cover 6. In addition, an optical sensor constituted by a light-emitting diode (LED) 25 and a photodiode (PD) 26 which oppose each other is mounted at the entrance of the through hole 24. When light emitted from the light-emitting diode 25 is blocked upon mounting of the chip guide and the chip in the through hole 24, the photodiode 26 detects the passage of an object and outputs a passage detection signal.

A cup-like guide member 27 is fixed on the inner side of the cover 6, and a through hole 28 is formed in the bottom end of the guide member 27 to oppose the through hole 24. An O-ring 29 is fitted on the inner peripheral portion of the through hole 28. A conical chip guide 30 is mounted in the through holes 24 and 28 and the O-ring 29.

The chip guide 30 is formed of a material which does not allow transmission of light, and has a hollow portion in which a chip member 43 to be mounted on the distal end of the luminous reagent syringe 42 is inserted. With this arrangement, the hollow portion of the chip guide 30 opposes the upper opening of the micro-sample tube 21 while the concave portion of the holder 16 is closed by the cover 6. In addition, the chip guide 30 is stably held in the through holes 24 and 28 due to the clamping force of the O-ring 29. The chip guide 30 is detachably mounted in the through holes 24 and 28 so that the chip guide 30 can be replaced with a new chip guide 30 or properly cleaned to be reused.

An optical sensor 31 is mounted on one end of the holder 16. The optical sensor 31 optically detects the open/closed state of the cover 6 and outputs a open/closed state detection signal. This signal is supplied to the controller 41 (to be described later) together with a passage detection signal from the photodiode 26.

The arrangement of the photo-sensing mechanism β will be described next. The photo-sensing mechanism β includes a cylindrical hollow chamber 33 having a cylindrical space 32 communicating with the space 20 via the through hole 22 formed in the bottom surface of the holder 16. A rotating cylindrical member 370 (including a metal column member 34) having a space for housing the micro-sample tube 21 is arranged in the hollow chamber 33. Note that the space of the cylindrical hollow chamber 33 is designed to have a volume large enough to prevent contact of the side wall of the micro-sample tube 21.

A lower end (the metal column member 34) of the rotating cylindrical hollow chamber 370 located in the cylindrical hollow chamber 33 to be rotatable in the circumferential direction is supported by a bearing mechanism 35, and the bearing mechanism 35 is coupled to the driving shaft of a driving motor 36 mounted on the lower portion of the cylindrical hollow chamber 33. With this arrangement, the rotating cylindrical hollow chamber 370 is driven by the driving motor 36 to be rotated in the circumferential direction within the hollow space 32 of the cylindrical hollow chamber 33 without being brought into contact with the side wall of the micro-sample tube 21. Note that the lower end of the micro-sample tube 21 is brought into contact with the bottom portion of the hollow chamber 32 with a small area. However, since this contact surface corresponds to the rotation center of the rotating cylindrical hollow chamber 370, the micro-sample tube 21 does not move upon rotation of the rotating cylindrical hollow chamber 370.

Openings 37 and 38 are respectively formed at one side of the side wall of the rotating cylindrical hollow chamber 370 and one side of the side wall of the cylindrical hollow chamber 33 to oppose the lower side portion of the micro-sample tube 21. When the rotating cylindrical hollow chamber 370 is rotated, the openings 37 and 38 coincide with each other only at a predetermined timing, but the opening 38 of the cylindrical hollow chamber 33 is closed by the side wall of the rotating cylindrical hollow chamber 370 at other timings.

An optical sensor 39 is mounted on one side of the cylindrical hollow chamber 33. The optical sensor 39 optically detects insertion of the micro-sample tube 21 and supplies the insertion detection signal to the controller 41. The cylindrical hollow chamber 33 has a sealed structure for preventing leakage of external light into the hollow space 32. That is, the cylindrical hollow chamber 33, the cover 6, the holder 16, and the like realize a so-called dark box for preventing leakage of external light into the hollow space 32 in which the micro-sample tube 21 is housed.

A high-sensitivity photo-sensing unit 40 is fixed on the outer side of the cylindrical hollow chamber 33 such that the imaging plane opposes the opening 38. The photo-sensing unit 40 has a photomultiplier 401 for photomultiplying and detecting feeble light received via the opening 38. For example, a sensor R-647-04 or R5610 available from Hamamatsu Photonics can be used as the sensor device in the photo-sensing unit 40. A signal output from the photo-sensing unit 40 is transmitted to the controller 41 incorporating a microcomputer system.

The coupling portion between the cylindrical hollow chamber 33 and the photo-sensing unit 40 is also sealed to prevent incidence of external light. Further, in the coupling portion, a filter for transmitting light of a predetermined wavelength is provided.

Figure 9:
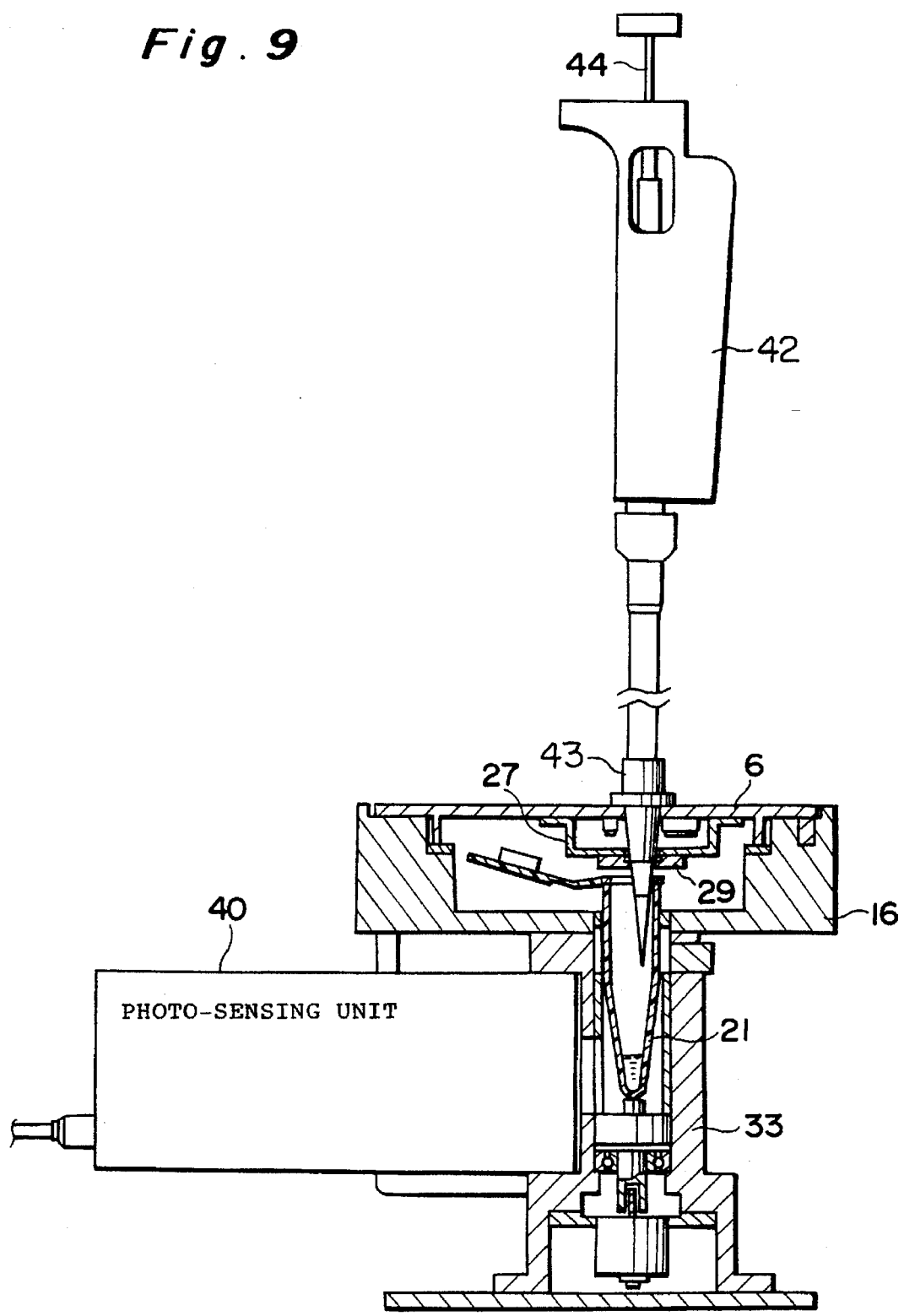
FIG. 9 is a view for explaining an operation in performing quantitative analysis by using the apparatus of the embodiment in correspondence with FIG. 8.

An operation procedure in the use of the above apparatus will be described next with reference to FIGS. 8 and 9. The same reference numerals in FIG. 9 denote the same or corresponding parts as in FIG. 8. FIG. 9 shows a state wherein the chip member 43 mounted on the distal end of the luminous reagent syringe 42 is inserted in the hollow portion of the chip guide 30.

A typical operation procedure will be described below. First of all, the cover 6 is opened, and the micro-sample tube 21 containing a sample solution M is inserted in the hollow space 32 of the cylindrical hollow chamber 33 via the through hole 22 of the holder 16.

The cover 6 is then closed, and the chip guide 30 is mounted in the through holes 24 and 28. Note that the chip guide 30 may be mounted in the through holes 24 and 28 in advance.

Subsequently, as shown in FIG. 9, the chip member 43 mounted on the distal end of the luminous reagent syringe 42 is inserted in the hollow portion of the chip guide 30. In this case, the chip member 43 has a cassette-like structure in which a predetermined type of luminous reagent is stored in advance. In addition, the chip member 43 has a conical outer shape to be fitted in the hollow portion of the chip guide 30. Furthermore, the chip guide 30 consists of a material which does not transmit light. By operating an operation rod 44 of the luminous reagent syringe 42, the luminous reagent can be injected from the distal end portion of the chip guide 30 into the micro-sample tube 21. As shown in FIG. 9, when the chip member 43 is mounted, the hollow portion of the chip guide 30 is sealed, thereby preventing incidence of external light into the hollow space 32 of the cylindrical hollow chamber 33 via the hollow portion of the chip guide 30.

The operation state is displayed on the liquid crystal display 13 on the basis of the above passage detection signal, open/closed state detection signal, and insertion detection signal. With this display 13, the user confirms that no external light leaks into the hollow space 32 of the cylindrical hollow chamber 33, and instructs to start the photo-sensing mechanism β.

In accordance with this instruction, the driving motor 36 is operated to rotate the rotating cylindrical hollow chamber 370. When the openings 37 and 38 coincide with each other, the photo-sensing unit 40 starts detection. If these openings 37 and 38 do not coincide with each other, a so-called shutter is closed.

In addition, by transferring a signal output from the photo-sensing unit 40 to the liquid crystal panel via the controller 41, a change over time can be displayed in real time.

In such an observed state, the operation rod 44 of the luminous reagent syringe 42 is operated to pour a predetermined amount of luminous reagent stored therein into the micro-sample tube 21, and light emitted from the sample solution M is detected.

As described above, according to the present invention, even with a very simple apparatus structure, luminescence from the sample solution M can be reliably imaged so that a high-precision quantitative analysis can be performed. In addition, monitor observation can be performed before the luminous reagent is mixed with the sample solution M, and luminescence can be observed in real time immediately after the mixing operation. Therefore, even a sample solution M which causes luminescence for only a short duration can be easily measured. Furthermore, measurement can be performed while the mixing amount of luminous reagent is properly adjusted. In particular, fine adjustment of the mixing amount can be performed by the above monitor observation. Contamination and the like caused by the sample solution M can be completely and easily prevented by only replacing or cleaning the micro-sample tube 21, the chip guide 30, and the chip member 43 as needed. As described above, this embodiment can provide many excellent effects in the field of quantitative analysis.

For example, this embodiment can be applied to quantitative analysis of ATP (adenosine triphosphate) which exists in an organism cell and serves to store and carry energy. The ATP amount in a living cell is constant. However, the ATP amount in a dead cell decreases because of autolysis. Therefore, a dead cell count can be analyzed by imaging luminescence of a specific wavelength which occurs when a predetermined type of luminous reagent is mixed with a sample solution M containing cells, and measuring the luminescence amount (or count). In addition, in measuring such an ATP amount, a luciferin-luciferase reaction represented by luminescence from a firefly may be used. More specifically, when luciferin is coupled with ATP in the presence of luciferase and magnesium to produce AMP (adenosine monophosphate) upon dephosphorization, the luciferin is excited to cause luminescence having a peak intensity at 562 nm. By measuring this luminescence, quantitative analysis of ATP can be performed.

By measuring ATP using this embodiment, measurement of a viable cell count in food such as milk or juice, a sterility test on an injection, measurement of a bacterium count in urine in a clinical bacterium test, or the like can be easily performed.

As has been described above, according to the present invention, the problems posed in the prior art can be completely solved.

The detachable chip guide is mounted on the upper portion of the dark box housing, and the chip member is mounted on this chip guide, thereby setting the inner space of the housing in a perfectly dark state. In this dark state, only luminescence from a sample solution is detected by the photo-sensing unit. With this simple structure, a reduction in the size of the apparatus can be easily realized.

In addition, since the chip guide and the chip member can be replaced with new ones, contamination of the apparatus can be prevented, and the luminous reagent can be easily replaced with a desired luminous reagent to realize a quick measurement process. As is apparent, since the problem of contamination by deposits can be solved, accurate, high-precision measurement can be realized. Since the amount of luminous reagent mixed with a sample solution can be finely adjusted by operating the reagent syringe, delicate quantitative analysis or the like can be easily performed.

As described above, the present invention exhibits excellent effects with the structure disclosed in the specification.

From the invention thus described, it will be obvious that the invention may be varied in many ways. Such variations are not to be regarded as a departure from the spirit and scope of the invention, and all such modifications as would be obvious to one skilled in the art are intended to be included within the scope of the following claims.

What is claimed is:

1. An apparatus for measuring chemiluminescence, comprising:
   a housing having an opening at a top surface thereof;
   a cover provided at the top surface of said housing, said cover having a through hole which allows a distal end of a first vessel containing a luminous reagent to be introduced from an outside of said housing into an interior of said housing;
   a hollow chamber disposed in said housing and having an opening at a side wall thereof, said hollow chamber having an inner space which allows a second vessel for containment of a sample solution to be partially housed by said hollow chamber;
   a holder disposed in said housing and enclosing the opening of said housing, said holder having an indented portion which defines a first space with said cover and which has a through hole connecting the first space to the inner space of said hollow chamber at a bottom surface of the indented portion;
   a photo-sensing unit disposed in said housing, for detecting luminescence from the second vessel in said housing via the opening of said hollow chamber;
   a shutter mechanism for optically shielding luminescence from the second vessel in said housing; and
   a device for holding the first vessel at a predetermined position, said device being disposed in the first space and having a through hole which allows the distal end of the first vessel to be partially introduced into the second vessel in said housing, a diameter of the through hole of said device being smaller than that of the through hole of said cover.

2. An apparatus according to claim 1, further comprising:
   a guide member disposed in the first space and contacting said cover for defining a second space with said cover, said guide member having a through hole which allows the distal end of the first vessel to be introduced into the second vessel;
   a photodiode provided in the second space; and
   a laser emitting diode provided in the second space.

3. An apparatus according to claim 2, further comprising:
   a hollow guide which is detachably mountable in the through holes of said cover and said guide member;
   wherein the first vessel comprises a member attached to a predetermined portion of the first vessel, whereby
   said hollow guide and attached member seal said housing when said hollow guide is in contact with said attached member by introducing the distal end of the first vessel via said hollow guide into the interior of said housing.

4. An apparatus according to claim 1, wherein said housing, said cover, said hollow chamber, said holder and said guide member are made of nontransparent material.

5. An apparatus according to claim 1, further comprising a first optical sensor for detecting a presence or absence of the second vessel, said first optical sensor being mounted to receive light passing through the side wall of said hollow chamber.

6. An apparatus according to claim 1, further comprising an optical sensor for detecting an open or closed state of said cover, said optical sensor being disposed at a portion facing said cover, the portion included in the indented portion of said holder.

7. An apparatus according to claim 1, further comprising a seal member for supporting the second vessel, said seal member being mounted at the opening of said holder.

8. An apparatus according to claim 1, wherein said shutter mechanism comprises:
   a rotatable hollow chamber for holding the second vessel at a predetermined position while partially housing the second vessel therein, said rotatable hollow chamber being disposed in said hollow chamber and having an opening at a side wall thereof; and a rotator for rotating said rotatable hollow chamber, said rotator being disposed in said hollow chamber while holding said rotatable hollow chamber.

9. An apparatus according to claim 8, wherein said rotatable hollow chamber is made of nontransparent material.

10. An apparatus for measuring chemiluminescence, comprising:

a housing having an opening at a top surface thereof;

a cover provided at the top surface of said housing, said cover having a through hole which allows a distal end of a first vessel containing a luminous reagent to be introduced from an outside of said housing into an interior of said housing;

a hollow chamber disposed in said housing and having an opening at a side wall thereof, said hollow chamber having an inner space which allows a second vessel for containment of a sample solution to be partially housed by said hollow chamber;

a holder disposed in said housing and enclosing the opening of said housing, said holder having an indented portion for forming a first space defined with said cover and having a through hole connecting the first space to the inner space of said hollow chamber at a bottom surface of the concave portion; and a shutter mechanism for optically shielding luminescence from the second vessel in said housing, said shutter mechanism including:

a rotatable hollow chamber for holding the second vessel at a predetermined position while partially housing the second vessel therein, said rotatable hollow chamber disposed in said hollow chamber and having an opening at a side wall thereof; and a rotator for rotating said rotatable hollow chamber, said rotator being disposed in said hollow chamber while holding said rotatable hollow chamber; and a photo-sensing unit for detecting luminescence from the second vessel in said housing via the openings of said hollow chamber and said rotatable hollow chamber.

11. An apparatus according to claim 10, further comprising a device for holding the first vessel at a predetermined position, said device being disposed in the first space and having a through hole which allows the distal end of the first vessel to be partially introduced into the second vessel, a diameter of the through hole of said device being smaller than a diameter of the through hole of said cover.

12. An apparatus according to claim 10, further comprising:

a guide member disposed in the first space and contacting said cover for defining a second space with said cover, said guide member having a through hole which allows the distal end of the first vessel to be introduced into the second vessel;

a photodiode provided in the second space; and a laser emitting diode provided in the second space.

13. An apparatus according to claim 12, wherein said housing, said cover, said hollow chamber, said holder and said rotatable hollow chamber are made of nontransparent material.

14. An apparatus according to claim 12, further comprising:

a guide being supported by the through hole of said cover and said guide member;

wherein the first vessel comprises a member attached to a predetermined portion of the first vessel, whereby said guide and attached member seal said housing when said guide is in contact with said attached member by introducing the distal end of the first vessel into the interior of said housing.

15. An apparatus according to claim 10, further comprising a first optical sensor for detecting a presence or absence of the second vessel, said first optical sensor mounted to receive light passing through the side wall of said hollow chamber.

16. An apparatus according to claim 10, further comprising an optical sensor for detecting an open state or a closed state of said cover, said optical sensor being disposed at a portion facing said cover, the portion included in the indented portion of said holder.

17. An apparatus according to claim 10, further comprising a seal member for supporting the second vessel, said seal member being mounted at the opening of said holder.

* * * * *